United States Patent [19]
Talmore

[11] Patent Number: 5,707,401
[45] Date of Patent: Jan. 13, 1998

[54] APPARATUS FOR AN EFFICIENT PHOTODYNAMIC TREATMENT

[75] Inventor: Eli T. Talmore, Haifa, Israel

[73] Assignee: ESC Medical Systems, Ltd., Yokneam, Israel

[21] Appl. No.: 394,238

[22] Filed: Feb. 24, 1995

[30] Foreign Application Priority Data

Mar. 10, 1994 [IL] Israel ............................ 108918

[51] Int. Cl.$^6$ .................................................. A61N 5/06
[52] U.S. Cl. .................................... 607/88; 606/3; 606/16
[58] Field of Search ........................ 607/88–93; 606/2, 606/3, 9, 10, 11, 12, 13, 16, 17, 18; 250/495.1

[56] References Cited

U.S. PATENT DOCUMENTS

| | | |
|---|---|---|
| 4,298,005 | 11/1981 | Mutzhas . |
| 5,036,242 | 7/1991 | Huber et al. . |
| 5,285,363 | 2/1994 | Meuse . |
| 5,344,434 | 9/1994 | Talmore . |

FOREIGN PATENT DOCUMENTS

| | | |
|---|---|---|
| 4112275 | 4/1991 | Germany . |
| 09850 | 5/1994 | WIPO . |

OTHER PUBLICATIONS

S. Kimmel et al., Lasers in Surgery and Medicine, vol. 2, No. 4, 1992, pp. 432–440.

*Primary Examiner*—Lee S. Cohen
*Assistant Examiner*—Eric F. Winakur
*Attorney, Agent, or Firm*—Morgan & Finnegan LLP

[57] ABSTRACT

The present invention relates to an improved apparatus for a therapeutic treatment of malignant solid tumors, consisting of a combined photodynamic therapy and hyperthermic treatment, said apparatus comprising a lamp possessing a narrow beam light, a mirror, an optical glass lenses system, a dicroic filter, a glass fiber optics bundle and an effective air-cooling system. This apparatus provides the administration of between 100 to 150 mw/cm$^2$ of red radiation in the range of between 600 to 750 nm band at a temperature of up to 46° C. Clinical results from three different hospitals show that by using this apparatus a success of more than 85% was achieved even after one single treatment.

6 Claims, 4 Drawing Sheets ns mechanisms for the synergism of PDT and HPT, were suggested which can be concluded as follows:

The PDT treatment increases the heat sensitivity of the tumor cells, due to a decrease of the pH.

The HPT enhances the photosensitization due to an increased blood flow.

The damage repair inactivation by each of the modalities enhances another effect.

Among other disadvantages of the heat and unwanted light, it should be mentioned the failure which might occur to the lamp, to the optical and electronics elements as well as the hazards to the operating personnel of the apparatus.

There are some prior patents which deal with the problem of cooling means, such as Xenon lamps, in order to decrease the disadvantages involved by their use. Thus, U.S. Pat. No. 4,298,005, suggests using a ventilator for cooling the housing of the apparatus.

U.S. Pat. No. 5,036,242, suggests using liquid-cooled lamp, having a passage for the flow of the liquid coolant and a passage for heated fluid outlet; the liquid-air heat exchanger is positioned in the flow circuit conduit by heat exchange with air.

U.S. Pat. No. 5,285,363, suggests using a method and device for removing heat generated from a Xenon-lamp, by using a heat transfer unit which is located adjacent to a mirror positioned in the path of the beam to transmit infra-red light.

The above brief review of the prior art clearly indicates the long felt need for an improved apparatus to deal with the subject of the present invention.

It is an object of the present invention to provide an improved apparatus for an efficient treatment of tumors which overcomes the disadvantages of the known apparatus. It is another object of the present invention to provide an improved apparatus for an efficient treatment of tumors wherein the unwanted light is removed while the generated heat is dissipated.

APPARATUS FOR AN EFFICIENT PHOTODYNAMIC TREATMENT

The present invention relates to an apparatus for invivo treatment of tumors. More particularly, the invention relates to an improved apparatus for an efficient photodynamic therapy as an in-vivo treatment of tumors.

BACKGROUND OF THE INVENTION

Photodynamic Therapy (hereinafter referred to as PDT), is recognised as a useful treatment for certain solid tumors, including skin cancer and internal organs such as colon, vagina, bladder and others. PDT treatment is based on a systemic or topical administration of a tumor-localizing photosensitizer reagent, such as porphirin, aminolevulinic acid (ALA), phtalocyanin, chlorine etc., which after illumination and excitation with visible light in the presence of oxygen, gives rise to highly reactive and cytotoxic singlet molecular oxygen which leads to tumor regression (see FIG. 1). In our previous U.S. Pat. No. 5,344,434, an apparatus for a PDT treatment was described. The apparatus comprises the following components:

- a Xe-lamp possessing a narrow beam light with half angle divergence of up to 10° possessing an intensity of at least 2 mW/nm with a special region in the range of 610 to 750 nm;
- a glass lense to focus the beam of the light;
- a red filter to provide a spectral region of above 610 nm;
- a 45° dichroic mirror to remove produced heat, and
- a light guide in the range of 3 to 12 mm diameter, which provides a minimum irradiance of 50 mW/cm$^2$.

The apparatus described in the above patent was found to be useful with a wide variety of photosensitizers contrary to what is claimed in some prior patent applications such as German 411 2275 41 and PCT 94/09850, that a narrow band filtering, does enable excitation of specific photosensitizers only. In addition to that, the broad band excitation mentioned in the invention described in our above prior U.S. patent, enables utilization of PDT photo-products, having an absorption maxima extended by 30 to 50 nm from the absorption maxima of the photosensitizer.

The Xe short arc and metal halide short arc lamps are most preferred, being able to produce the arc image of the highest radiance. However, these lamps are very inefficient generators of spectral energy. Thus, with a Xe lamp of 300 W input electrical energy only about 50 W are transformed into light, i.e., from ultra-violet to near infra-red, while the other 250 W are transformed into heat. The available spectral intensity in the spectral interval of 100 nm bandwidth is only 5 W. Therefore, in order to produce a spectrally filtered intensity, 45 W of undesired light must be filtered out. In this manner, the overall balance shows that only 2% of the electrical input are transformed into the desired spectral output, while the balance of 295 W of heat and unwanted light is most undesirable.

It is also known that PDT involves damage to the tumor vascular bed, which in turn causes disruption of tumor blood flow and ultimately to a tissue necrosis. The vascular damage produced by the PDT treatment in the tumor, reduces its efficiency in cooling the tumor. Hyperthermia or heating of the tumor to the moderate temperature of up to 46° C. has been proven to be of clinically value. It has been published (S. Kimmel et. al, Lasers & Surgery medicine, 12: 432–440, 1992) that a combination of PDT with Hyperthermic therapy (hereafter referred to HPT) will result a 40% decrease of the irradiation dose required to produce vascular damage. Vari-

BRIEF DESCRIPTION OF THE INVENTION

The invention relates to an efficient apparatus for a therapeutic treatment of malignant solid tumors, consisting of a combined photodynamic therapy and hyperthermic therapy which comprises:

A lamp possessing an narrow beam light;

a "hot" mirror;

an optical glass lens system;

a dichroic filter having at least 60% transmittance above 600 nanometers.

a glass fiber optics bundle, and an effective air-cooling system to provide an internal temperature in the apparatus of not above 46° C.

DETAILED DESCRIPTION OF THE INVENTION

Hyperthermia has been proven to be selectively lethal to various malignant cells in the range of 41° to 46° C., thus being considered to be of a clinical value. According to the present invention, it was found that the combination of PDT and HPT when applied simultaneously, is much more effective and provides better results than the two separate individual treatments. The benefit from this combination, besides the decrease of about 40% of the irradiation dose required to produce vascular damage is also a better penetration.

The photochemical reaction enhancement at elevated temperatures which results from the PDT, produces a strong cytotoxic effect and reduces the required treatment dosage. On the other hand, the thermal penetration depth in the tissue which is generally in the range of 3 to 7 nm, is higher than the optical penetration of between 1 to 3 mm at 630 nm. Therefore, shallow tumors might be treated by PDT alone, but an efficient treatment could not be achieved in case of deeper tumors.

It was found that the apparatus according to the present invention, produces a moderate heating of the tumor to a temperature in the range of between 41° to 46° C. and most preferably to about 45° C. This effect called hyperthermia, imparts a synergistic effect when combined with the PDT treatment. As a result, the overall efficiency in treating deep tumors is greatly enhanced.

According to a most preferred embodiment, the treatment will consist from the administration of between 100 to 150 mw/cm$^2$ of red radiation in the range of between 600 to 750 nm band and simultaneously a heating of the tumor to a temperature of up to 46° C. The total time of treatment will be about 20 minutes, including only about 5 minutes of pure PDT, reaching the above maximum temperature and a simultaneous HPT treatment for about 15 minutes.

Figure 4:
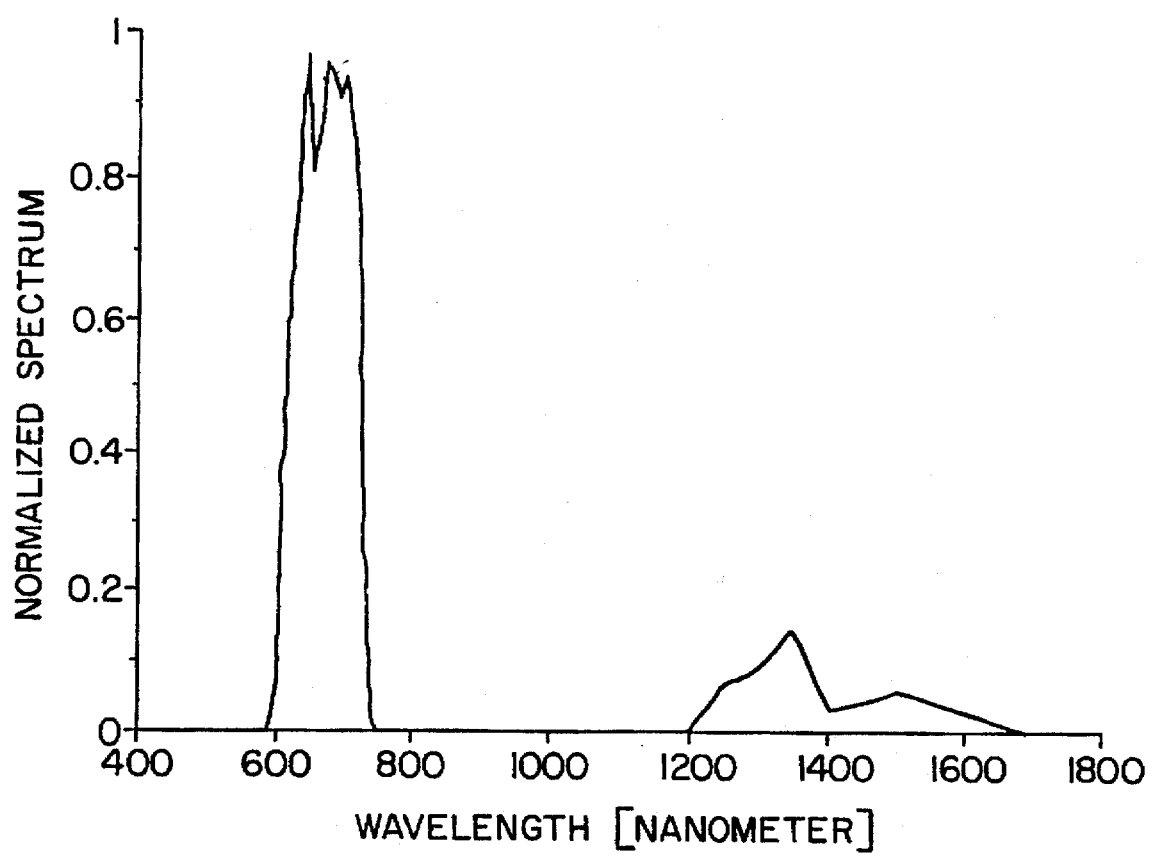
FIG. 4 illustrates the spectral distribution preferred embodiment.

The hyperthermal treatment may be obtained by a direct heating of the tumor. However, for a better control of the maximum temperature produced, an optical irradiation is preferred. For example, by a simultaneous irradiation at 1.2 to 1.7 um, the required heating of a tumor could be produced with a irradiance of only 30 to 70 mw/sq.cm. for a period of about 20 minutes. A preferred apparatus according to the present invention is characterized by a simultaneous illumination in the range of between 600 to 750 nm in the "red" and between 1200 to 1700 nm in the near infra-red. The ratio between the power emitted in the "red" to the power emitted in the near Infra-red is preferably between 2:1 and 5:1 and most preferably between 3:1. A preferred mode for applying the heating is by a $CO_2$ laser or NdYaG laser. The resulting spectrum of the preferred embodiment is shown in FIG. 4.

DETAILED DESCRIPTION OF THE FIGURES

Figure 1:
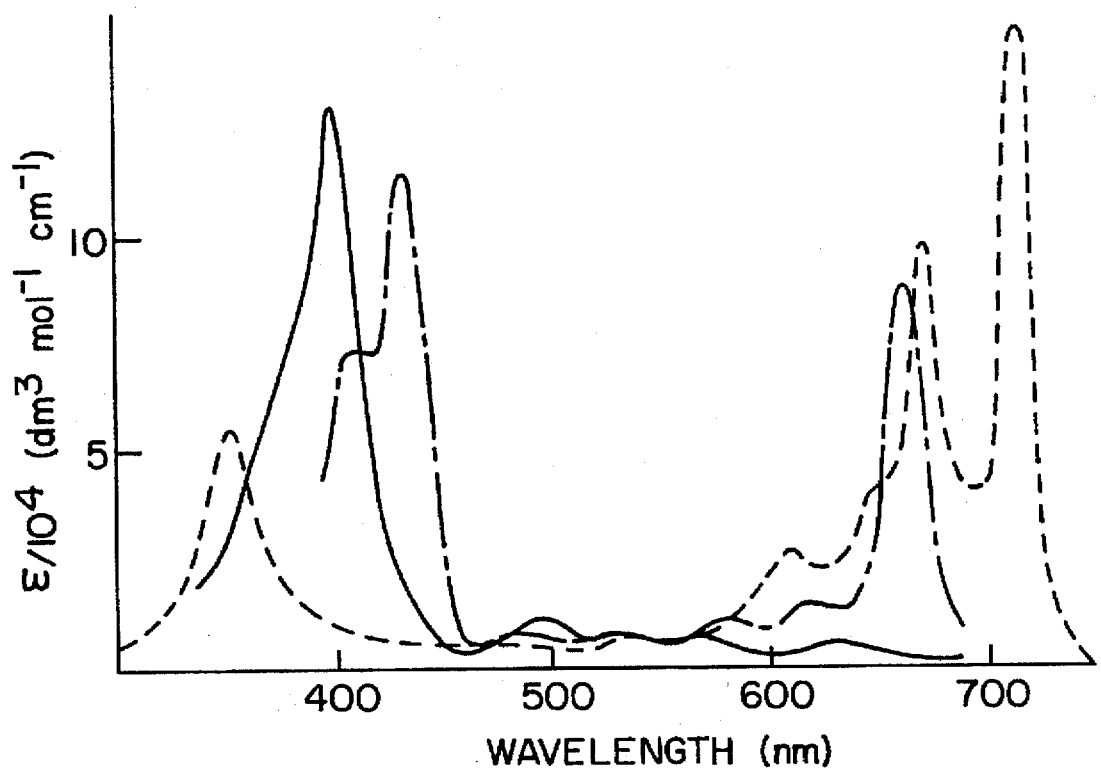
FIG. 1 illustrates a typical absorption spectra of photosensitizers.

FIG. 1, illustrates typical absorption spectra of monomeric porphyrin, chlorins and phthalocyanines.

Figure 2:
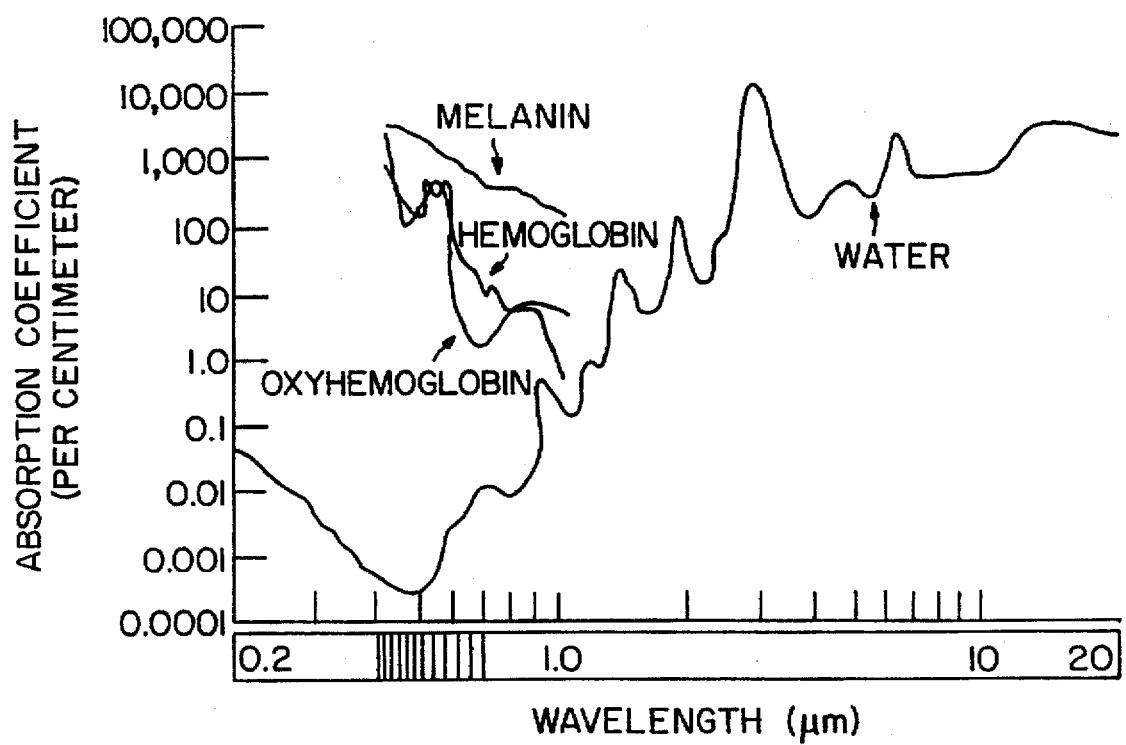
FIG. 2 illustrates a typical absorption spectra of tissue constituents.

FIG. 2, illustrates typical absorption spectra of melanin, hemoglobin, oxyhemoglobin and water which involves the mechanisms for the synergistic effect which may include several contributions.

Figure 3:
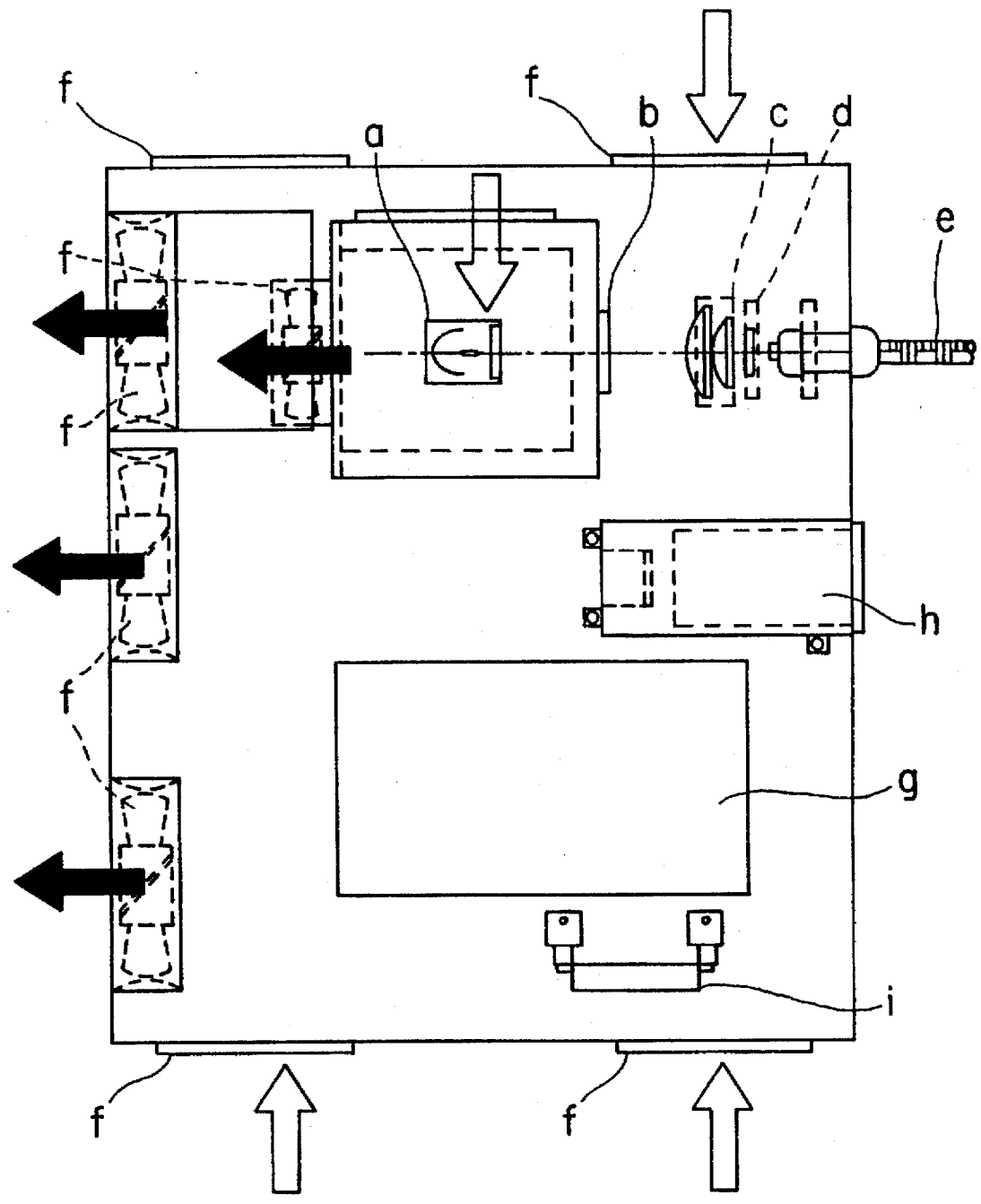
FIG. 3 is a schematic illustration of the improved apparatus according to the present invention which combines the PDT and HPT treatments of solid tumor.

FIG. 3, describes the apparatus according to the present invention which comprises the following main components:
  (a) A lamp possessing a narrow beam light with half angle divergence of up to 10°, having an intensity of at least 20 mW/nm at a spectral region in the range of 600 to 750 nm and intensity of at least 2 mW/nm in the spectral region of 1200 to 1700 nm.
  (b) A "hot"mirror", comprising a hard all-dielectric filter coating deposited on a borosilicate glass (commercially available under the tradename TEMPAX™ form Scott America), having a transmittance of at least 60% in the range of 600 to 750 nm and at least 5% in the range of 1200 to 1700 nm range, while reflecting the radiation between the 750 to 1200 nm range. According to a preferred embodiment, the angle of the mirror relative to the axis may be varied in order to change the ratio of the transmittance in those two bands.

The ratio between the transmittance at the 600 to 750 nm and 1200 to 1700 nm may be changed by rotating the mirror from its axis, between 0° and 45° relative to the optical axis.
  (c) An optical glass lenses system to focus the beam of the light, preferably with a broad band Anti-Reflection coating for the visible spectrum. comprising a hard all-dielectric coating.
  (d) A dichroic filter comprising a hard all-dielectric coating having at least 60% transmittance above 600 nm.
  (e) A glass fiber optics bundle, having an input diameter in the range of 1 to 12 mm, preferably 6 mm and length of 0.5 m to 2.5 m and most preferably 1.5 m, as a separate unit or as a part of endoscope.
  (f) An effective air-cooling system for the removal of the unwanted light and dissipation of the generated heat, so that the internal temperature in the apparatus will not exceed 50° C. According to a preferred embodiment, this cooling is obtained by two or more fans, which provides an internal temperature in the apparatus of not above 46° C. The most preferred embodiment includes 4 fans to dissipate hot air and an inlet system for ambient air.
  (g) A power supply;
  (h) A timer to control the length of exposure.
  (i) An electronic control card.

FIG. 4, illustrates the "red" dual band spectral distribution, correlating the normalized spectrum as a function of wavelength (in nanometers).

From FIG. 2, the following conclusions can be drawn:
  The absorption of oxyhemoglobin in the 600–750 nm range does result in a temperature increase which causes an increase in molecular oxygen concentration due to dissociation. This effects counter the effect of oxygen depletion during the PDT.
  The absorption of hemoglobin in the blood vessels is in the range of 600 to 750 nm,which produces an increase in the temperature and an enhanced PDT reaction rate.
  The clinical results in three different hospitals using the apparatus according to the present invention for skin cancer treatments of 150 patients, show a success of 85% even after one single treatment.

The apparatus according to the present invention, also can be incorporated in other systems, thus providing additional useful functions as known in the art. Thus for instance, by adding a violet filter in the range of 400–450 nm, using the means of the filter wheel, it could be used for excitation of photosensitizers in photodynamic diagnostics. On the other hand, the incorporation of a green filter in the spectral range of 505–590 nm using the means of the filter wheel, may be used for superficial PDT treatment or for various dermatologic applications such as removal of tatoos and portwine stains.

The addition of distal hand-piece to the fiber optics bundle for dermatologic application, will enable a substantially uniform illumination of up to 3 cm diameter tumors.

Fluorescence spectrometer enabling real-time fluorescence measurements excited by violet filter, can be used for cancer diagnostics known in the aft as "optical biopsy".

Other functions which could incorporate the apparatus according to the present invention are:

Endoscopes for different applications, such as colon, bronchi, gastro, etc.

RGB (red-green-blue) and CCD (charge-coupled-device) cameras to provide multi-spectral vieweing through the above endoscopes.

The addition of white filter in the spectral range of between 400 to 700 nm using the means of the filter wheel may be used for the endoscopic observation.

The apparatus was found also to be used with a broad types of photosensitizers as known in the art and also when narrow band filters enable excitation of only specific photosensitizers. Furthermore, the broad band excitation used in the present invention, enables the utilization of PDT photoproducts, having the absorption maxima removed by 30 to 50 nm from the absorption maxima of the photosensitizer used.

While the invention has been described and illustrated in respect to some particular features, it should be understood that the description does not limit it, a person skilled in the art after reading the present specification, will be in a position to insert slight modifications, without being outside the invention as covered by the appended claims. Thus for example, modifications to the electronic components: g, h and i, (see FIG. 3) will enable pulsed high power operations of the above device in dermatological applications such as removal of portwine stains and tattoos.

I claim:

1. An apparatus for an efficient simultaneous photodynamic and hyperthermic treatment, said apparatus having an optical axis, said apparatus comprising:

a. a lamp for emitting a narrow beam light with half angle divergence of up to 10°, having an intensity of at least 20 mW/nm of red radiation in the spectral region of 600 to 750 nm and at least 2 mW/nm of infrared radiation in the spectral region of 1100 to 1700 nm, said lamp generating heat when emitting said beam light;

b. a "hot" mirror, comprising a hard, all-dielectric filter coating deposited on a borosilicate glass, having a transmittance of at least 60% between 600 and 750 nm and at least 5% between 1200 and 1700 nm, while reflecting the radiation between 750 and 1200 nm;

c. a glass lens system, optionally having an anti-reflection coating;

d. a dichroic filter made of a hard, all-dielectric coating deposited on glass, having at least 60% transmittance above 600 nm while having a negligible transmittance below 600 nm;

e. a glass fiber optics bundle having a diameter between 1 and 12 mm as a separate unit or as part of an endoscope; said elements a–e being aligned along the optical axis of the apparatus; and f. an effective air-cooling system to decrease the internal heating of the apparatus, which provides an internal temperature in the apparatus below a maximum temperature of 50° C.

2. The apparatus according to claim 1, wherein the angle of said hot mirror relative to the optical axis may be varied in order to change the ratio of transmittance in the two radiation ranges.

3. The apparatus according to claim 1, wherein said air-cooling system comprises at least two fans which provides an internal temperature in the apparatus of not above 45° C.

4. The apparatus according to claim 1, wherein the ratio between power emitted in the 600–750 nm red radiation region to power emitted in the 1100–1700 nm Infra-red radiation region is between 2:1 to 5:1.

5. The apparatus according to claim 1, wherein the heating of step (a) is obtained by irradiation of said lamp in the range of between 1.2 to 1.7 µm.

6. The apparatus according to claim 1, wherein said heating of step (a) is obtained by a $CO_2$, laser or Nd:YAG laser.

* * * * *